(12) United States Patent
Tojo et al.

(10) Patent No.: US 10,716,638 B2
(45) Date of Patent: Jul. 21, 2020

(54) ROBOT SYSTEM

(71) Applicants: KAWASAKI JUKOGYO KABUSHIKI KAISHA, Kobe-shi, Hyogo (JP); MEDICAROID CORPORATION, Kobe-shi, Hyogo (JP)

(72) Inventors: Tsuyoshi Tojo, Ibaraki (JP); Nobuyasu Shimomura, Kobe (JP)

(73) Assignees: KAWASAKI JUKOGYO KABUSHIKI KAISHA, Kobe-Shi (JP); MEDICAROID CORPORATION, Kobe-Shi (JP)

(*) Notice: Subject to any disclaimer, the term of this patent is extended or adjusted under 35 U.S.C. 154(b) by 385 days.

(21) Appl. No.: 15/755,479

(22) PCT Filed: Jun. 24, 2016

(86) PCT No.: PCT/JP2016/003063
§ 371 (c)(1),
(2) Date: Feb. 26, 2018

(87) PCT Pub. No.: WO2017/033378
PCT Pub. Date: Mar. 2, 2017

(65) Prior Publication Data
US 2018/0243908 A1    Aug. 30, 2018

(30) Foreign Application Priority Data
Aug. 25, 2015    (JP) ................................ 2015-165479

(51) Int. Cl.
*G06F 17/00*    (2019.01)
*A61B 34/37*    (2016.01)
(Continued)

(52) U.S. Cl.
CPC .............. *A61B 34/37* (2016.02); *A61B 34/32* (2016.02); *B23P 19/04* (2013.01); *B23Q 15/12* (2013.01);
(Continued)

(58) Field of Classification Search
CPC ... A61B 34/32; G06T 7/62; G06T 7/70; B23P 19/04; B23Q 15/12; B25J 3/00;
(Continued)

(56) References Cited

U.S. PATENT DOCUMENTS 4,967,127 A * 10/1990 Ishiguro ................. B25J 13/085
                                                        318/570
5,116,180 A      5/1992 Fung et al.
(Continued)

FOREIGN PATENT DOCUMENTS

JP    S56-39884 A    4/1981
JP    H07-194609 A   8/1995
(Continued)

OTHER PUBLICATIONS

Kuchenbecker et al. "Induced Master Motion in Force-Reflecting Teleoperation." Journal of Dynamic Systems, Measurement, and Control, Dec. 1, 2006, pp. 1-6, XP055581061, DOI: 10.1115/1.2364011, Retrieved from the Internet: URL:https://www.seas.upenn.edu/"kuchenbe/pub/pdf/Kuchenbecker06-JDSMC-Induced.pdf. [Retrieved on Apr. 15, 2019].
(Continued)

*Primary Examiner* — Ronnie M Mancho
(74) *Attorney, Agent, or Firm* — Oliff PLC

(57)   ABSTRACT

Robot system includes robot main body including robot arm, end effector attached to robot arm, and force sensing device detecting force applied to end effector's tip end, actual reaction-force information generator generating force-sensing information according to force detected by force sensing
(Continued)

device, and output force-sensing information as actual reaction-force information, virtual reaction-force information generator outputting force component detected by force sensing device, that has a magnitude proportional to time differentiation value, as virtual reaction-force information, adder configured to output information obtained by adding actual reaction-force information outputted from actual reaction-force information generator to virtual reaction-force information outputted from virtual reaction-force information generator, as synthetic reaction-force information, operating device outputting, when operator is made to sense a force according to synthetic reaction-force information outputted from adder and operator operates, operating information according to operation, and motion controller controlling robot main body's operation according to operating information outputted from operating device.

9 Claims, 6 Drawing Sheets

(51) Int. Cl.
| | |
|---|---|
| G05B 19/418 | (2006.01) |
| B25J 9/00 | (2006.01) |
| B23P 19/04 | (2006.01) |
| B25J 13/00 | (2006.01) |
| B25J 19/04 | (2006.01) |
| B25J 9/16 | (2006.01) |
| B25J 13/08 | (2006.01) |
| B25J 3/00 | (2006.01) |
| B25J 13/06 | (2006.01) |
| B25J 18/00 | (2006.01) |
| B25J 19/02 | (2006.01) |
| B25J 3/04 | (2006.01) |
| B23Q 15/12 | (2006.01) |
| B25J 13/02 | (2006.01) |
| B25J 11/00 | (2006.01) |
| G06F 3/01 | (2006.01) |
| H04N 5/232 | (2006.01) |
| H04N 7/18 | (2006.01) |
| A61B 34/32 | (2016.01) |
| G06T 7/62 | (2017.01) |
| G06T 7/70 | (2017.01) |
| B23P 21/00 | (2006.01) |

(52) U.S. Cl.
CPC . *B25J 3/00* (2013.01); *B25J 3/04* (2013.01); *B25J 9/0081* (2013.01); *B25J 9/0084* (2013.01); *B25J 9/0087* (2013.01); *B25J 9/161* (2013.01); *B25J 9/1602* (2013.01); *B25J 9/163* (2013.01); *B25J 9/1612* (2013.01); *B25J 9/1628* (2013.01); *B25J 9/1633* (2013.01); *B25J 9/1646* (2013.01); *B25J 9/1653* (2013.01); *B25J 9/1664* (2013.01); *B25J 9/1669* (2013.01); *B25J 9/1674* (2013.01); *B25J 9/1682* (2013.01); *B25J 9/1689* (2013.01); *B25J 9/1697* (2013.01); *B25J 11/008* (2013.01); *B25J 13/00* (2013.01); *B25J 13/003* (2013.01); *B25J 13/006* (2013.01); *B25J 13/02* (2013.01); *B25J 13/025* (2013.01); *B25J 13/06* (2013.01); *B25J 13/065* (2013.01); *B25J 13/08* (2013.01); *B25J 13/084* (2013.01); *B25J 13/085* (2013.01); *B25J 13/087* (2013.01); *B25J 13/088* (2013.01); *B25J 18/00* (2013.01); *B25J 19/023* (2013.01); *B25J 19/028* (2013.01); *B25J 19/04* (2013.01); *G05B 19/4182* (2013.01); *G06F 3/017* (2013.01); *G06T 7/62* (2017.01); *G06T 7/70* (2017.01); *H04N 5/23219* (2013.01); *H04N 7/181* (2013.01); *B23P 21/00* (2013.01); *B23P 21/002* (2013.01); *G05B 2219/33007* (2013.01); *G05B 2219/35464* (2013.01); *G05B 2219/37297* (2013.01); *G05B 2219/39004* (2013.01); *G05B 2219/39102* (2013.01); *G05B 2219/39439* (2013.01); *G05B 2219/39531* (2013.01); *G05B 2219/39533* (2013.01); *G05B 2219/40022* (2013.01); *G05B 2219/40134* (2013.01); *G05B 2219/40136* (2013.01); *G05B 2219/40139* (2013.01); *G05B 2219/40142* (2013.01); *G05B 2219/40143* (2013.01); *G05B 2219/40145* (2013.01); *G05B 2219/40146* (2013.01); *G05B 2219/40161* (2013.01); *G05B 2219/40162* (2013.01); *G05B 2219/40163* (2013.01); *G05B 2219/40169* (2013.01); *G05B 2219/40182* (2013.01); *G05B 2219/40183* (2013.01); *G05B 2219/40195* (2013.01); *G05B 2219/40387* (2013.01); *G05B 2219/40627* (2013.01); *Y10S 901/02* (2013.01); *Y10S 901/03* (2013.01); *Y10S 901/08* (2013.01); *Y10S 901/09* (2013.01); *Y10S 901/10* (2013.01); *Y10S 901/27* (2013.01); *Y10S 901/41* (2013.01); *Y10S 901/46* (2013.01); *Y10S 901/47* (2013.01)

(58) Field of Classification Search
CPC . B25J 3/04; B25J 9/0081; B25J 9/0084; B25J 9/0087; B25J 9/1602; B25J 9/161; B25J 9/1612; B25J 9/1628; B25J 9/163; B25J 9/1633; B25J 9/1646; B25J 9/1653; B25J 9/1664; B25J 9/1669; B25J 9/1674; B25J 9/1682; B25J 9/1689; B25J 9/1697; B25J 11/008; B25J 13/00; B25J 13/003; B25J 13/006; B25J 13/02; B25J 13/025; B25J 13/06; B25J 13/065; B25J 13/08; B25J 13/084; B25J 13/085; B25J 13/087; B25J 13/088; B25J 18/00; B25J 19/023; B25J 19/028; B25J 19/04; G05B 19/4182; G05B 2219/33007; G05B 2219/35464; G05B 2219/37297; G05B 2219/39004; G05B 2219/39102; G05B 2219/39439; G05B 2219/39531; G05B 2219/39533; G05B 2219/40022; G05B 2219/40134; G06F 3/017; H04N 5/23219; H04N 7/181; B23P 21/00; B23P 21/002
USPC .......................................................... 700/248
See application file for complete search history.

(56) References Cited

U.S. PATENT DOCUMENTS

| | | | | |
|---|---|---|---|---|
| 6,142,581 | A * | 11/2000 | Yamaguchi | B60T 7/12 |
| | | | | 303/113.2 |
| 6,190,091 | B1 * | 2/2001 | Byle | B63B 21/00 |
| | | | | 405/195.1 |
| 8,723,472 | B2 * | 5/2014 | Takeuchi | G05B 19/404 |
| | | | | 318/135 |
| 9,290,905 | B1 * | 3/2016 | Diaz | E02F 3/188 |
| 2003/0114960 | A1 * | 6/2003 | Takenaka | B62D 57/02 |
| | | | | 700/245 |

(56) References Cited

U.S. PATENT DOCUMENTS

2004/0164697 A1* 8/2004 Iribe .................. B25J 13/088
                                                    318/568.12
2009/0216374 A1   8/2009 Low et al.

FOREIGN PATENT DOCUMENTS

| JP | 2006-102866 A | 4/2006 |
| JP | 2009-282720 A | 12/2009 |
| JP | 2011-224696 A | 11/2011 |
| JP | 2014-000655 A | 1/2014 |
| JP | 2014-148037 A | 8/2014 |
| TW | 200304608 A | 10/2003 |

OTHER PUBLICATIONS

Aug. 30, 2016 International Search Report issued in International Patent Application No. PCT/JP2016/003063.
May 16, 2017 Office Action issued in Taiwanese Patent Application No. 105127054.

\* cited by examiner

ROBOT SYSTEM

TECHNICAL FIELD

The present disclosure relates to a robot system.

BACKGROUND ART

Normally, when a human performs a work manually, since he/she can tactually sense a change in temperature etc. of the hand when the hand contacts an object to be worked as well as a reaction force against his/her hand, a highly-precise tactual sensing is possible. Conventionally, technologies which use tactual sensing information in robot systems are known. For example, Patent Document 1 discloses a robot system in which a mobile robot is operated while obtaining a force-sensor feedback between a joystick and the mobile robot. In recent years, the robot system is applied to various works which require high precision. Examples of applications include a fitting work of components, an inspecting work of a finished surface after machining, and a surgical operation system.

REFERENCE DOCUMENT OF CONVENTIONAL ART

Patent Document

[Patent Document 1] JP2009-282720A

DESCRIPTION OF THE DISCLOSURE

Problems to be Solved by the Disclosure

However, in the conventional robot system described above, the tactual sensing information which can be fed back to an operating device end is limited to the reaction force. Thus, when such a robot system is applied, for example, to the surgical operation system, it is difficult to sensitively sense that a surgical instrument attached to a tip end of the robot contacts a patient's affected part. Therefore, there is room for an improvement in operability. Such a problem is common to the cases where the robot system is applied to those works which require high precision, such as the fitting work of components and the inspecting work of a finished surface after machining.

Thus, the purpose of the present disclosure is to improve an operability of work which requires high precision in a robot system.

SUMMARY OF THE DISCLOSURE

According to one aspect of the present disclosure, a robot system is provided, which includes a robot main body including a robot arm, an end effector attached to the robot arm, and a force sensing device configured to detect a force applied to a tip end of the end effector, an actual reaction-force information generator configured to generate force-sensing information according to the force detected by the force sensing device, and output the force-sensing information as actual reaction-force information, a virtual reaction-force information generator configured to output a component of the force detected by the force sensing device, that has a magnitude proportional to a time differentiation value, as virtual reaction-force information, an adder configured to output information obtained by adding the actual reaction-force information outputted from the actual reaction-force information generator to the virtual reaction-force information outputted from the virtual reaction-force information generator, as synthetic reaction-force information, an operating device configured to output, when an operator is made to sense a force according to the synthetic reaction-force information outputted from the adder and the operator operates, operating information according to the operation, and a motion controller configured to control operation of the robot main body according to the operating information outputted from the operating device. Here, the force detected by the force sensing device includes forces in each direction of three axis which are perpendicular to each other and moment acting about each axis.

With this configuration, when the force sensing device detects the force applied to the tip end of the end effector in the robot main body, the actual reaction-force information generator generates the force-sensing information according to the force detected by the force sensing device, and outputs the force-sensing information as the actual reaction-force information. Here, the virtual reaction-force information generator outputs the component of the force detected by the force sensing device, that has a magnitude proportional to a time differentiation value, as the virtual reaction-force information. Then, the operating device makes the operator sense the force according to the synthetic reaction-force information outputted from the adder. The operator grasps the force according to the synthetic reaction-force information, and operates the operating device based on the grasped force according to the synthetic reaction-force information so as to operate the robot to make the robot perform an appropriate work. Then, the operating device outputs the operating information according to this operation, and the motion controller controls the operation of the robot according to the operating information. Thus, since the operator senses a strong reaction force for a moment from the operating device when the tip end of the end effector contacts an object to be worked, he/she can sense the contact sensitively and is possible to perform highly-precise work.

The robot main body may be a slave arm and the operating device may be a master arm, and the slave arm may be remotely controlled by the master arm.

The force sensing device may be attached to a base end of the end effector, and may be a force sensor configured to detect a force applied to the tip end of the end effector.

The robot system may further include a mode selector configured to be selectable of any one of operating modes of the motion controller to control the operation of the robot main body. The operating modes may include an automatic mode in which the operation of the robot main body is controlled using a given preset program, without reflecting the operating information in the operation of the robot main body, a correctable automatic mode in which the operation of the robot main body is controlled using the given preset program, while the operating information is reflectable in the operation of the robot main body, and a manual mode in which the operation of the robot main body is controlled using the operating information without using the given program. When the operating mode is the correctable automatic mode, the motion controller may control the robot main body to perform operation corrected from the operation related to the given program, in response to the operating information while the robot main body operates using the given program.

With this configuration, since the automatic mode is selectable by the mode selector as the operation mode of the motion controller, when the operation of the robot is not necessary to be corrected, the automatic mode is selected. In this manner, it is prevented that the operating device is unnecessarily operated to correct the operation. Further, since the manual mode is selectable by the mode selector as the operation mode of the motion controller, the robot main body is operated without using the given program.

The robot system may be applied to a surgical operation system, and the end effector may be a surgical instrument.

With this configuration, an operator senses sensitively that the surgical instrument contacts a patient's affected part in the surgical operation system, and is possible to perform the highly precise operation. The surgical instrument may be forceps, endoscope, etc.

Effect of the Disclosure

According to the present disclosure, the operability of the work which requires high precision in the robot system is improved.

The purpose, other purposes, features, and advantages of the present disclosure will be apparent from the following detailed description of suitable embodiments with reference to the accompanying drawings.

MODES FOR CARRYING OUT THE DISCLOSURE

Figure 1:
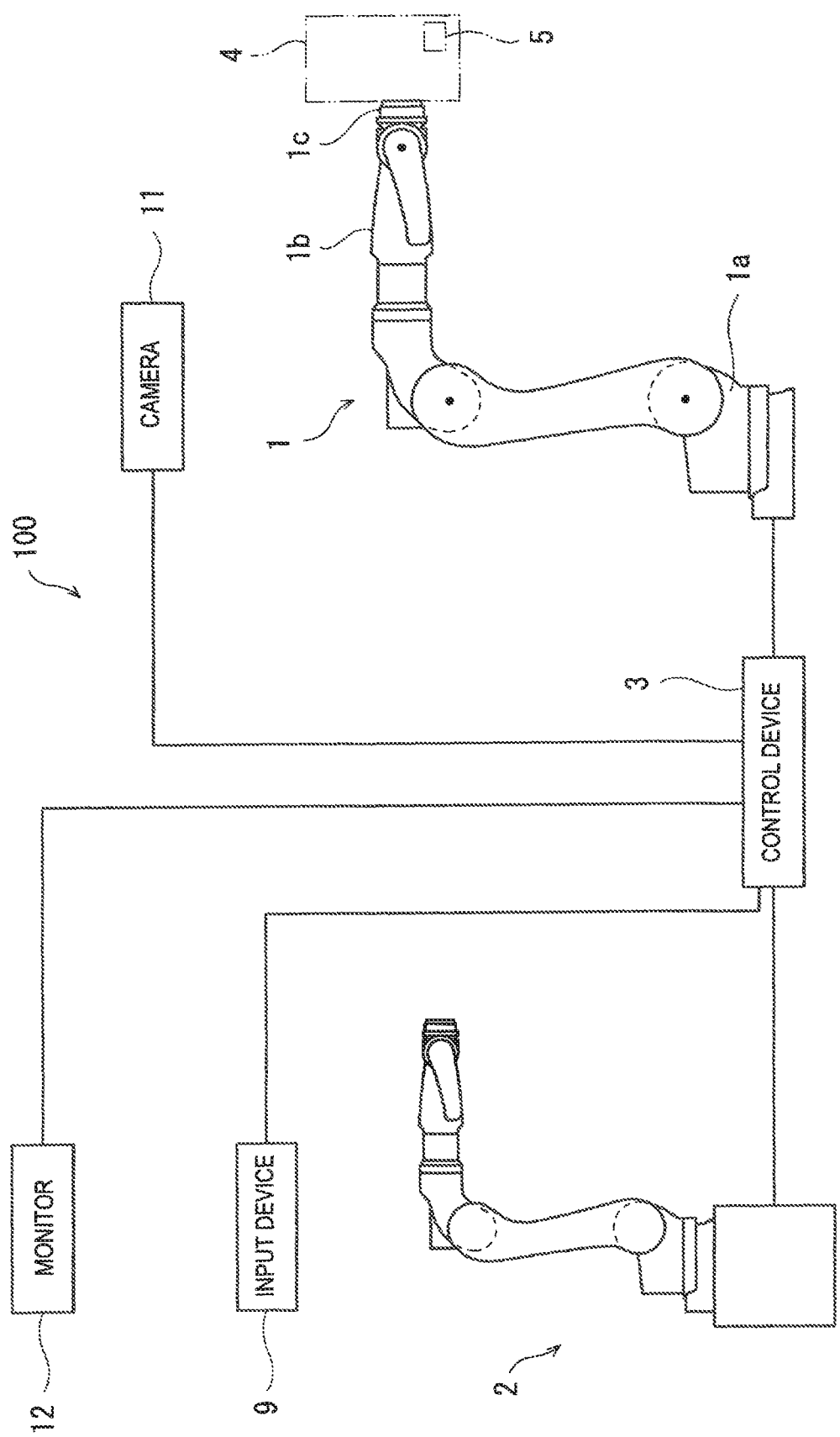
FIG. 1 is a schematic diagram illustrating one example of a configuration of a robot system according to a first embodiment.

Hereinafter, embodiments according to the present disclosure will be described with reference to the accompanying drawings. Below, the same reference characters are assigned to the same or corresponding components throughout the drawings to omit redundant description.

First Embodiment

FIG. 1 is a schematic diagram illustrating one example of a configuration of a robot system according to a first embodiment of the present disclosure. As illustrated in FIG. 1, a robot system 100 of this embodiment is comprised of a master-slave type remote control system in which a slave arm 1 is remotely controlled by a master arm 2.

The robot system 100 (hereinafter, referred to as "the remote control system") includes the slave arm 1 comprised of a first robot, the master arm 2 comprised of a second robot, a control device 3, a force sensor 5, an input device 9, a camera 11, and a monitor 12. The slave arm 1 may be comprised of a robot of any type. The slave arm 1 corresponds to a "robot main body" of the present disclosure. In this embodiment, the slave arm 1 is, for example, comprised of a well-known articulated robot, and includes a pedestal 1a, an articulated or multi joint arm 1b provided to the pedestal 1a, and a hand part 1c provided to a tip end of the arm 1b. Each joint of the articulated arm 1b includes a driving servo motor, an encoder which detects a rotation angular position of the servo motor, and a current sensor which detects current flowing into the servo motor (none of them is illustrated). An end effector 4 is attached to the hand part 1c, and the force sensor 5 is attached to the end effector 4.

The master arm 2 may be comprised of a robot of any type. The master arm 2 corresponds to an "operating device" of the present disclosure. Although in this embodiment the master arm 2 has a similar structure to the slave arm 1, the master arm 2 may be, for example, a switch, an adjustment knob, a control lever, or a mobile terminal, such as a tablet, or may be a simple device, such as a joystick, as long as the operating device can operate the slave arm 1 by an operator operating it. When the operator operates the master arm 2 to operate the slave arm 1, the master arm 2 transmits operating information according to the operation, to the control device 3.

The input device 9 is comprised of a man-machine interface, such as a touch panel or a keyboard. The input device 9 is mainly used in order to input switching among three modes, an automatic mode, a correctable automatic mode, and a manual mode of the slave arm 1 (described later), as well as various data, etc. The information inputted into the input device 9 is transmitted to the control device 3.

In the remote control system 100, the operator who is located at a position distant from a workspace of the slave arm 1 (outside the workspace) moves the master arm 2 so that the operating information is inputted, to cause the slave arm 1 to perform an operation corresponding to the operating information. As a result, a specific work can be performed. Moreover, in the remote control system 100, the slave arm 1 is also capable of automatically performing a given work, without the operator operating the master arm 2.

Herein, the operating mode in which the slave arm 1 is operated according to the operating information inputted via the master arm 2 is referred to as "the manual mode." Note that "the manual mode" also includes a case where part of the operation of the slave arm 1 which is under operation based on the operating information inputted by the operator operating the master arm 2, is automatically corrected. Moreover, the operating mode in which the slave arm 1 is operated according to a given preset program is referred to as "the automatic mode."

Further, the remote control system 100 of this embodiment is configured so that, while the slave arm 1 operates automatically, the operation to be carried out automatically is correctable by reflecting the operation of the master arm 2 to the automatic operation of the slave arm 1. Herein, the operating mode in which, while the operating information inputted via the master arm 2 is reflectable, the slave arm 1 is operated according to the given preset program is referred to as "the correctable automatic mode." Note that "the automatic mode" described above is distinguished from "the correctable automatic mode" in that the operation of the master arm 2 is not reflected in the operation of the slave arm 1 when the operating mode in which the slave arm 1 is operated is the automatic mode.

The camera 11 is provided so as to be able to image the operation of the slave arm 1 within all or part of a movable range of the slave arm 1. Image information imaged by the camera 11 is transmitted to the control device 3, and the control device 3 controls the monitor 12 so as to display an image corresponding to the image information.

Figure 2:
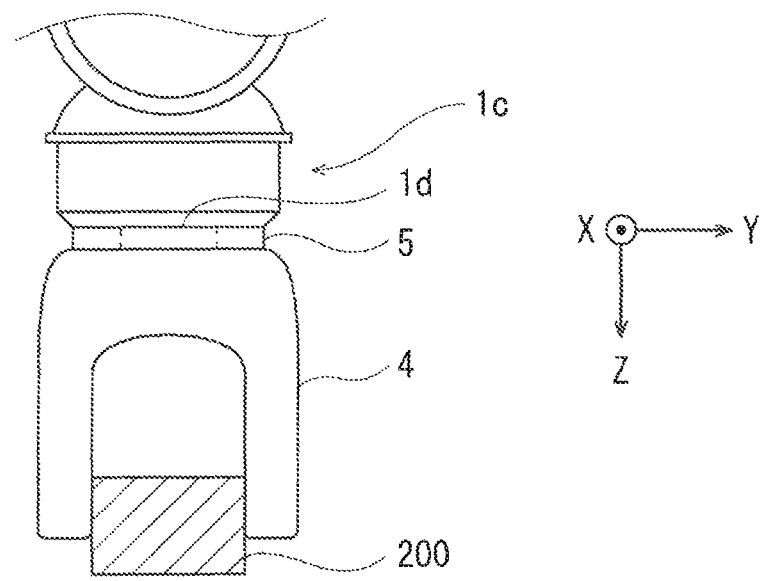
FIG. 2 is a schematic diagram illustrating one example of a configuration of a tip end of a slave arm in FIG. 1.
Figure 2:
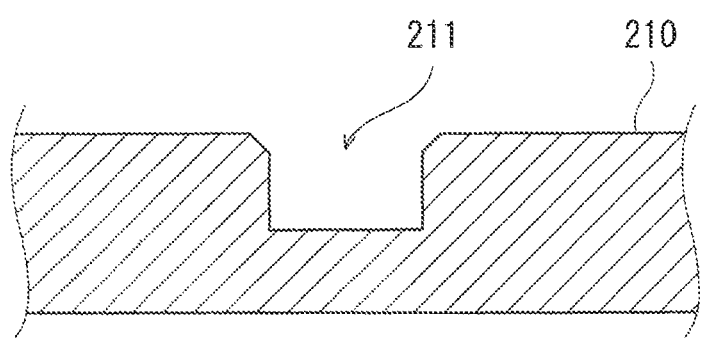

FIG. 2 is a schematic diagram illustrating one example of a configuration of a tip end of the slave arm 1. As illustrated in FIG. 2, the end effector 4 is attached to an attaching surface 1d at a tip end of the hand part 1c. In this embodiment, the end effector 4 is a robot hand capable of gripping a fitting component 200. The robot hand includes a hand main body attached to the attaching surface 1d at the tip end of the hand part 1c, and, two finger parts driven by an actuator (not illustrated) comprised of a motor, for example. When the actuator operates, the two finger parts move with respect to the hand main body. That is, the two finger parts of the robot hand are movable so as to approach or separate mutually, and the two finger parts are grippable of the fitting component 200. In the remote control system 100 of this embodiment, the fitting component 200 held by the robot hand (4) is precisely fitted into a hole 211 of a fitted component 210 by the operation of the slave arm 1. This fitting operation requires a skilled operator among assembling works.

The force sensor 5 is attached between the attaching surface 1d at the tip end of the hand part 1c and the end effector 4. The force sensor 5 corresponds to a "force sensing device" of the present disclosure. In this embodiment, the force sensor 5 is attached to a base end of the end effector 4, and it is configured so as to detect a force applied to a tip end of the end effector 4. The force sensor 5 is a 6-axis force sensor capable of detecting forces in the XYZ axis directions defined by a hand part coordinate system, and moment acting about each axis. Here, the hand part coordinate system is a coordinate system on the basis of the hand part 1c. In FIG. 2, X-axis and Y-axis are defined in parallel with the attaching surface 1d of the hand part 1c, and Z-axis is defined in a direction perpendicular to the attaching surface 1d. The force sensor 5 wirelessly or wiredly transmits a detection signal to the control device 3.

Figure 3:
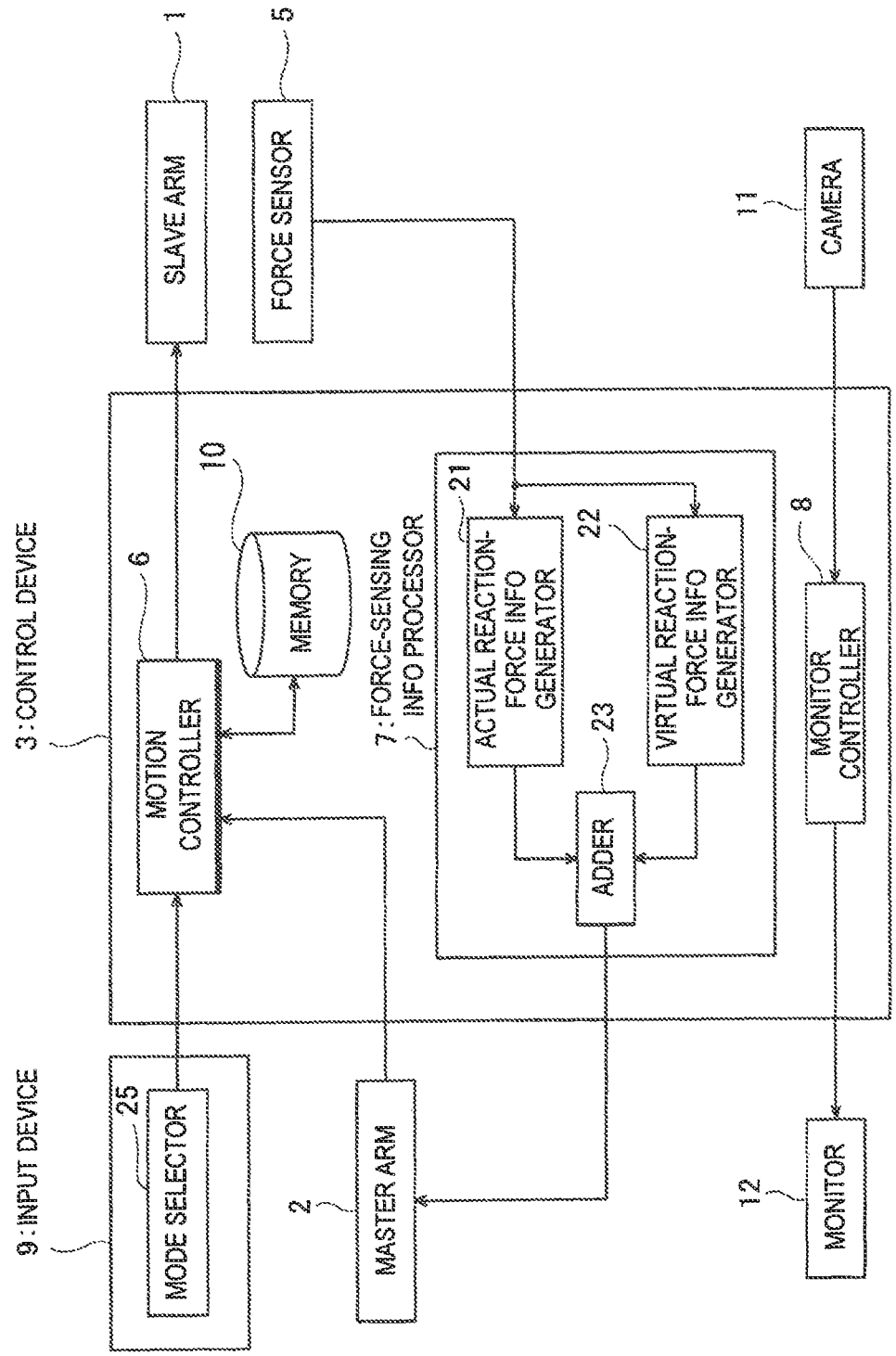
FIG. 3 is a block diagram illustrating a configuration of a control device in FIG. 1.

FIG. 3 is a block diagram illustrating a configuration of the control device 3. As illustrated in FIG. 3, the control device 3 includes a motion controller 6, a force-sensing information processor 7, a monitor controller 8, a memory 10, and an interface part (not illustrated). The control device 3 is comprised of a device having an arithmetic processing function, such as a computer, a micro controller, or a microprocessor. The motion controller 6, the force-sensing information processor 7, and the monitor controller 8 are implemented by an arithmetic processor (not illustrated) of the control device 3 executing a given program stored in the memory 10 of the control device 3. The hardware configuration of the control device 3 may be arbitrary, and the control device 3 may be provided independently from other devices, such as the slave arm 1, or may be provided integrally with other devices.

The motion controller 6 controls the operation of the slave arm 1 according to the information inputted from the input device 9 and the operating information transmitted from the master arm 2. Here, a mode selector 25 of the input device 9 is for the operator to select any one of "the automatic mode," "the correctable automatic mode," and "the manual mode" which are described above, as the operating mode in which the slave arm 1 is operated. Information on the mode selected by the operator is inputted into the motion controller 6 from the mode selector 25. The memory 10 is a readable and writable recording medium, and stores beforehand the given program for causing the slave arm 1 to automatically carry out a given operation. The given program is, for example, teaching information which is stored by a teaching work so that the slave arm 1 is operated to perform a given work. In this embodiment, the teaching information may be information which is stored by instructing the operation of the slave arm 1 by operating the master arm 2, or information which is stored by a direct instruction. Note that although the memory 10 is provided integrally with the control device 3, it may be provided separately from the control device 3. Specifically, the motion controller 6 controls the servo motor which drives each joint shaft of the slave arm 1 based on at least one of the operating information from the master arm 2 and the prestored information. The motion controller 6 generates a position instructing value for each joint shaft of the slave arm 1, and then generates a speed instructing value based on a difference between the generated position instructing value and the detection value (actually value) of the encoder. Then, the motion controller 6 generates a torque instructing value (current instructing value) based on a difference between the generated speed instructing value and a present speed value, and controls the servo motor based on a difference between the generated current instructing value and the detection value (actually value) of the current sensor.

The force-sensing information processor 7 includes an actual reaction-force information generator 21, a virtual reaction-force information generator 22, and an adder 23. The actual reaction-force information generator 21 generates the force-sensing information according to the force detected by the force sensor 5, and outputs this force-sensing information as actual reaction-force information. Here, the actual reaction-force information generator 21 is configured so that it acquires the detection signal of the force sensor 5, converts the force applied to the tip end of the robot hand (4) so that the force falls within an appropriate range, and outputs it to the adder 23 as an actual reaction force. The actual reaction-force information generator 21 may include a low-pass filter in order to remove noise.

The virtual reaction-force information generator 22 outputs a component of the force detected by the force sensor 5, which has a magnitude proportional to a time differentiation value of the detected force, as the virtual reaction-force information. Here, the virtual reaction-force information generator 22 is configured so that it acquires the detection signal of the force sensor 5, calculates the component of the force applied to the tip end of the robot hand (4), which has the magnitude proportional to the time differentiation value, and outputs it to the adder 23 as the virtual reaction-force information.

The adder 23 outputs information obtained by adding the actual reaction-force information outputted from the actual reaction-force information generator 21 to the virtual reaction-force information outputted from the virtual reaction-force information generator 22, as the synthetic reaction-force information. Here, the adder 23 is configured so that it adds the actual reaction-force information outputted from the actual reaction-force information generator 21 to the virtual reaction-force information outputted from the virtual reaction-force information generator 22, and outputs it to the master arm 2 as the synthetic reaction-force information. The synthetic reaction force is converted into a torque value of each joint of the master arm 2. The converted torque value corresponds to a torque command to a driver (driver circuit) of the actuator (not illustrated) which drives each joint. When the master arm 2 makes the operator sense the force corresponding to the synthetic reaction-force information outputted from the adder 23 and the operator operates the master arm 2, the master arm 2 outputs the operating information according to this operation to the motion controller 6.

The monitor controller 8 controls the monitor 12 so as to display the image corresponding to the image information which is imaged by the camera 11. The operator can operate the slave arm 1 as he/she intended by operating the master arm 2 while looking at the monitor 12.

Figure 4:
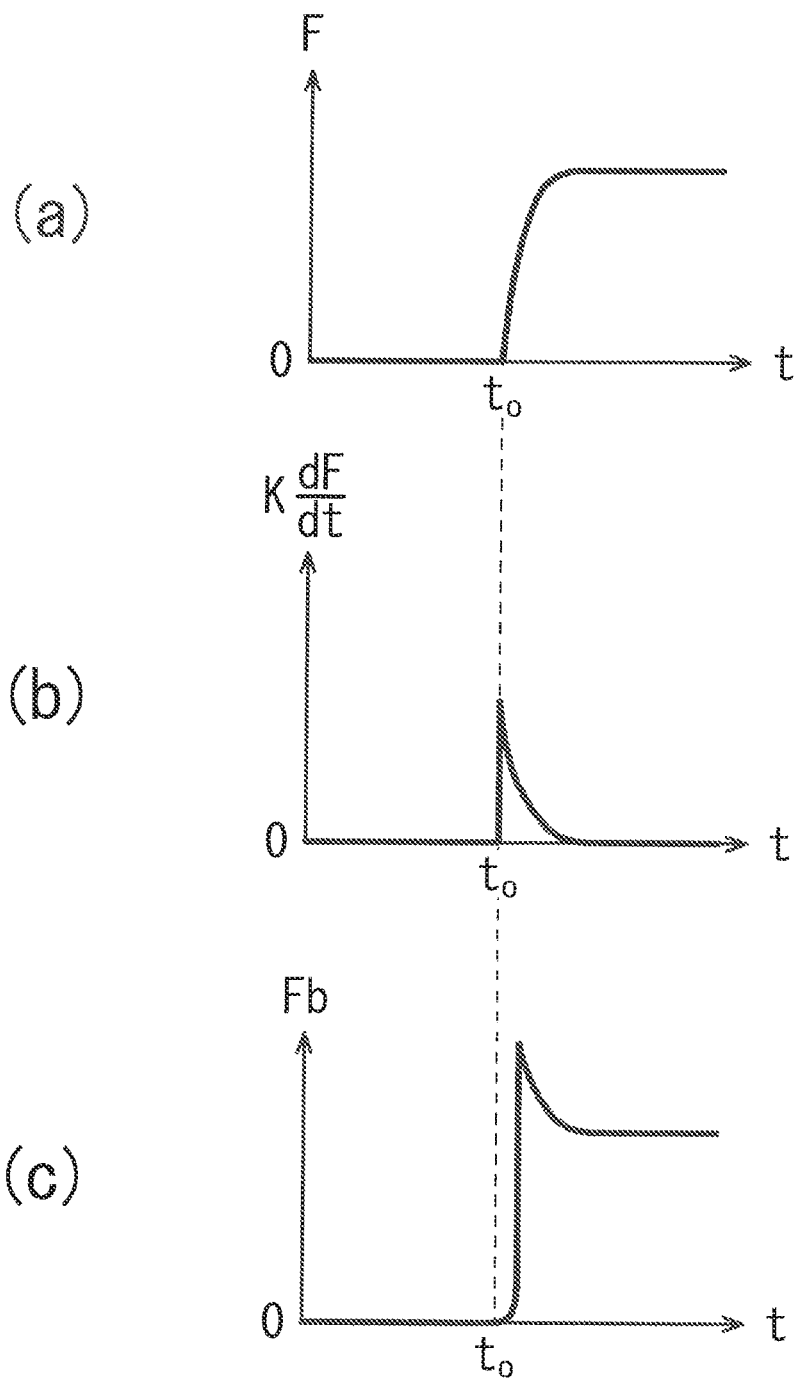
FIG. 4 illustrates graphs schematically illustrating time changes in an actual reaction force, a virtual reaction force, and a synthetic reaction force of these reaction forces, according to a force detected by a force sensor.

Next, operation of the remote control system 100 is described using FIGS. 2 to 4. In the remote control system 100 of this embodiment, the operator inserts the fitting component 200 held by the robot hand (4) into the hole 211 of the fitted component 210 by the operation of the slave arm 1, by operating the master arm 2 while looking at the monitor 12 (see FIG. 2). Here, a case where the operating mode selected by the operator using the mode selector 25 is "the manual mode" is described. When the operating mode in which the slave arm 1 is operated is "the manual mode," the motion controller 6 controls the operation of the slave arm 1 according to the operating information (input command) sent by operating the master arm 2, without using the given program (see FIG. 3). Meanwhile, the force sensor 5 attached to the tip end of the slave arm 1 detects the force applied to the tip end of the robot hand (4). The actual reaction-force information generator 21 generates the force-sensing information according to the force detected by the force sensor 5, and outputs this force-sensing information as the actual reaction-force information. The operator pushes down the robot hand (4) which grips the fitting component 200, toward the fitted component 210 (in the Z-direction of FIG. 2) by the operation of the slave arm 1, by operating the master arm 2 while looking at the monitor 12. As a result, the fitting component 200 held at the tip end of the robot hand (4) or by the robot hand (4) contacts the fitted component 210 or the hole 211 formed in the fitted component 210. FIG. 4(*a*) is a graph schematically illustrating a time change of the actual reaction force F according to the force detected by the force sensor 5. As illustrated in FIG. 4(*a*), immediately after starting the operation of the slave arm 1, the force applied to the tip end of the robot hand (4) is zero, but the force applied to the tip end of the robot hand (4) increases at the time to, and the actual reaction force F according to the force detected by the force sensor 5 also increases.

Meanwhile, the virtual reaction-force information generator 22 outputs the component of the force detected by the force sensor 5, which has the magnitude proportional to the time differentiation value, as the virtual reaction-force information. FIG. 4(*b*) is a graph schematically illustrating a time change of the virtual reaction force K(dF/dt). Here, K is a constant. As illustrated in FIG. 4(*b*), immediately after starting the operation of the slave arm 1, the virtual reaction force K(dF/dt) proportional to the time differentiation value of the force in detected by the force sensor 5 is zero. When the actual reaction force F according to the force detected by the force sensor 5 increases at the time to, the virtual reaction force rapidly increases accordingly, but it then rapidly decreases.

The adder 23 outputs to the master arm 2 information obtained by adding the actual reaction-force information outputted from the actual reaction-force information generator 21 to the virtual reaction-force information outputted from the virtual reaction-force information generator 22, as the synthetic reaction-force information. Then, the master arm 2 makes the operator sense the force according to the synthetic reaction-force information outputted from the adder 23. The operator grasps the force according to the synthetic reaction-force information, and operates the master arm 2 based on the grasped force according to the synthetic reaction-force information so as to operate the robot to make the robot perform an appropriate work. Then, the master arm 2 outputs the operating information according to this operation, and the motion controller 6 controls the operation of the robot according to the operating information.

FIG. 4(*c*) is a graph schematically illustrating a time change of the synthetic reaction force Fb. As illustrated in FIG. 4(*c*), when the fitting component 200 held at the tip end of the robot hand (4) or by the robot hand (4) contacts the fitted component 210 or the hole 211 formed in the fitted component 210 at the time t0, the synthetic reaction force Fb increases rapidly under the influence of the virtual reaction force K(dF/dt). Thus, since the operator senses a strong reaction force for a moment from the master arm 2, he/she can sense the contact sensitively and is possible to perform highly-precise work.

Second Embodiment

Next, a second embodiment is described. A basic configuration of a remote control system of this embodiment is similar to that of the first embodiment. Below, description of the configuration common to the first embodiment is omitted, and only different configuration is described.

Figure 5:
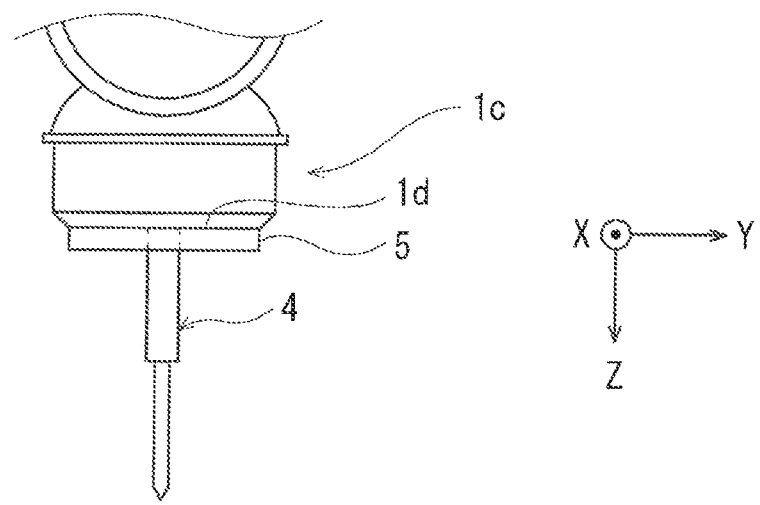
FIG. 5 is a schematic diagram illustrating a configuration of a robot system according to a second embodiment.
Figure 5:
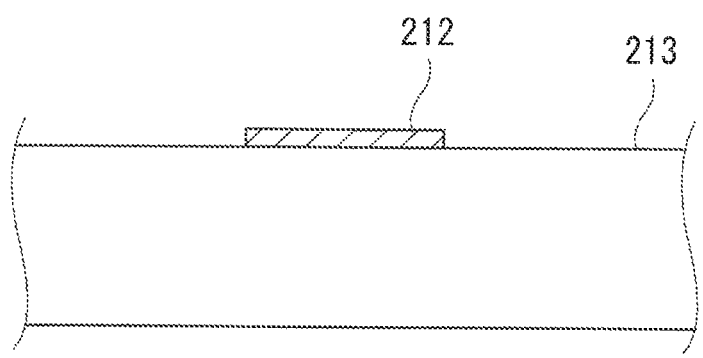

FIG. 5 is a schematic diagram illustrating the configuration of the remote control system of the robot according to the second embodiment. As illustrated in FIG. 5, this embodiment is different from the first embodiment in that the end effector 4 attached to the tip end of the hand part 1*c* of the slave arm 1 is a contact probe for measuring an electric resistance. The contact probe (4) has a needle type tip-end shape. Moreover, the force sensor 5 is also attached between the attaching surface 1*d* at the tip end of the hand part 1*c*, and the end effector 4. The remote control system of this embodiment measures the electric resistance of the surface of a measuring target object 212 fixedly disposed on a measurement table 213. A connection method of the resistance measurement is, for example, 2-terminal method or 4-terminal method. In the measurement, the tip end of the needle type contact probe (4) is contacted to the inspecting surface of the measuring target object 212 by the operation of the slave arm 1. If the measuring target object 212 is, for example, a component with low rigidity, such as a thin plate or a thin cylinder, deformation etc. is easy to be caused and, thus, the work in which the tip end of the very small needle is contacted to the surface of the measuring target object 212 requires a skilled operator.

When the operating mode selected in the mode selector 25 is "the manual mode," the operator operates the master arm 2 while looking at the monitor 12 so that the robot hand (4) to which the contact probe (4) is attached at the tip end thereof is pushed down toward the measuring target object 212 (in the Z-direction of FIG. 5) by the operation of the slave arm 1.

Even with the configuration of this embodiment, since the operator senses the strong reaction force for a moment at the moment of contact from the master arm 2 when the tip end of the contact probe (4) contacts the measuring target object 212, he/she is possible to sense the contact sensitively and to perform the highly-precise work.

Note that, although in the above embodiment describes the case where the operating mode selected in the mode selector 25 is "the manual mode," the operating mode selected in the mode selector 25 may be "the automatic mode." When the operating mode in which the slave arm 1 is operated is "the automatic mode," the motion controller 6 controls the operation of the slave arm 1 according to the given preset program without using the operating information sent from the master arm 2.

Moreover, the operating mode selected in the mode selector 25 may be "the correctable automatic mode." When the operating mode is "the correctable automatic mode," the motion controller 6 uses both the given program and the operating information. Note that, if the operating information has not been sent to the motion controller 6 while the operating mode is "the correctable automatic mode," the motion controller 6 uses only the given program. In more detail, when the operating mode in which the slave arm 1 is operated is "the correctable automatic mode," the motion controller 6 controls the operation of the slave arm 1 using both the given program and the operating information in response to the reception of the operating information while the slave arm 1 operates automatically using the given program. Thus, the slave arm 1 performs an operation related to the given program, i.e., an operation which is corrected from the operation to be performed automatically.

Note that in each of the above embodiments, although the motion controller 6 is configured so as to operate the slave arm 1 according to any one of the operating modes, "the automatic mode," "the correctable automatic mode," and "the manual mode," which is selected by the operator using the mode selector 25 of the input device 9, the present disclosure is not limited to such a configuration. For example, when the motion controller 6 controls the slave arm 1 to be operated in "the automatic mode" up to a given step, the motion controller 6 may have an output controller (not illustrated) which outputs to the operator an inquiry related to a permission of continuation of the automatic operation of the slave arm 1, and a continuation determinator (not illustrated) which determines whether the continuation of the automatic operation is to be permitted based on an input signal which is received by a receiver (not illustrated) after the inquiry is outputted by the output controller (not illustrated). Thus, in a scene which requires the skilled worker (e.g., the fitting work or the contacting work), the mode is switched from "the automatic mode" to "the manual mode" to perform the highly-precise work.

Third Embodiment

Next, a third embodiment is described. A basic configuration of a remote control system of this embodiment is similar to that of the embodiment described above. Below, description of a configuration common to the first embodiment is omitted, and description will be made focusing on different configurations. The remote control system of this embodiment is applied to a surgical operation system, and the end effector is a surgical instrument. The surgical operation system is a master-slave type operation support robot. Here, it is a system in which the operator, such as a doctor, performs an endoscope surgical operation to a patient.

Note that, since the surgical operation system of this embodiment is for operation support, the slave arm 1 is configured so as to operate only in "the manual mode." Thus, the input device 9 is not provided with the mode selector 25 for selecting the operating mode by the operator (see FIG. 3). The operator operates the master arm 2 while looking at the monitor 12 to operate the slave arm 1 as he/she intended. Illustration of a specific configuration of the master arm 2 is omitted.

Figure 6:
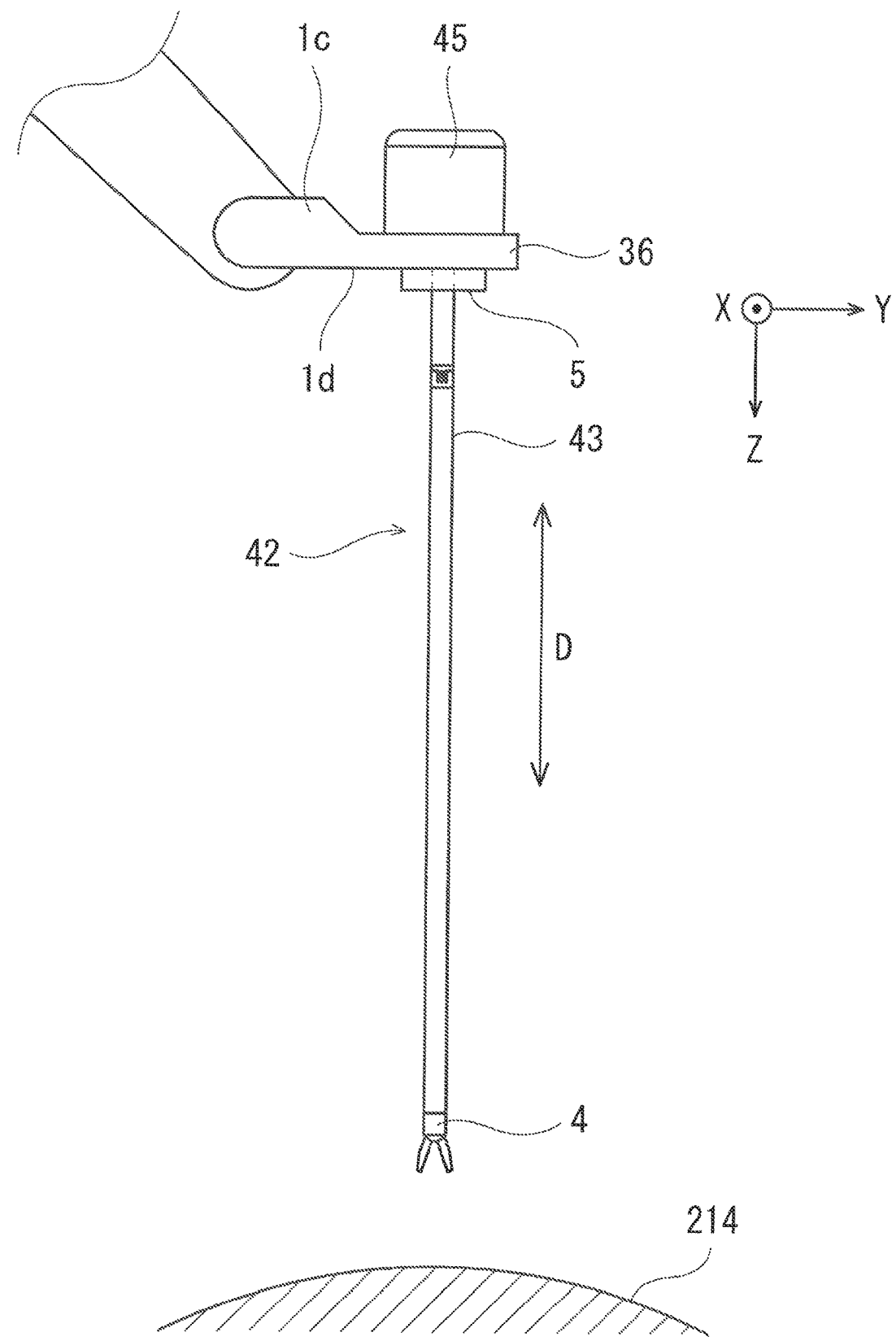
FIG. 6 is a schematic diagram illustrating a configuration of a robot system according to a third embodiment.

FIG. 6 is a schematic diagram illustrating the configuration of the remote control system of the robot according to the third embodiment. As illustrated in FIG. 6, a holder 36 (instrument holding part) which holds an instrument (surgical instrument) 42 is formed in the hand part 1c at the tip end of the slave arm 1. The force sensor 5 is attached between the attaching surface 1d (a back surface of the holder 36) of the hand part 1c at the tip end of the slave arm 1, and the instrument 42. The instrument 42 is held by the holder 36 so as to be attachable and detachable. A shaft 43 of the instrument 42 held by the holder 36 is configured so as to extend parallel with reference directions D. Note that an endoscope assembly may be held by the holder 36 so as to be attachable and detachable. In this embodiment, the operator operates the instrument 42 of the slave arm 1 by the operation of the slave arm 1.

The instrument 42 is comprised of a drive unit 45 provided to a base end part of the instrument 42, the end effector (surgical tool) 4 provided to a tip end part of the instrument 42, and the long and narrow shaft 43 which connects between the drive unit 45 and the end effector 4. The reference directions D is defined in the instrument 42, and the drive unit 45, the shaft 43, and the end effector 4 are aligned in parallel with the reference directions D. The end effector 4 of the instrument 42 is selected from a group comprised of a surgical instrument having an operable joint (e.g., forceps, scissors, a grasper, a needle holder, a microdissector, a staple applier, a tucker, a siphonage tool, a snare wire, a clip applier, etc.), and an instrument without a joint (e.g., a cutting blade, a cautery probe, a washer, a catheter, a suction orifice, etc.).

In a surgical operation system (100), various operations are performed to the patient 214 by the surgical instrument (4) at the tip end of the slave arm 1. Not only a general operation but the operation using the surgical operation system (100) also requires the skilled operator. Even with the configuration of this embodiment, since the operator senses a strong reaction force for a moment at the moment of contact from the master arm 2 when the surgical instrument (4) contacts the patient 214, he/she senses the contact sensitively and is possible to perform the highly precise operation.

Other Embodiments

Note that, although the remote control system 100 of each of the above embodiments is configured so that the force sensor 5 is provided with as the force sensing device, and the force applied to the tip end of the end effector is detected by the force sensor 5 (see FIGS. 2 and 3), the remote control system 100 is not limited to this configuration. For example, although the motion controller 6 controls the servo motor which drives each joint shaft of the slave arm 1 as described above, it may calculate the force acting on the tip end of the end effector 4 of the slave arm 1 based on at least one rate of change of a positional deviation, a speed deviation, and a current deviation for each joint shaft. Thus, effects equivalent to those of the above embodiments can be obtained with a simple configuration, without having the force sensor 5.

Moreover, although the robot system 100 of each of the above embodiments is comprised of the master-slave type remote control system, the robot system 100 is not limited to this configuration. For example, other robot systems may be configured so that they make people around or an administrator of the system sense the reaction force received from the object to be worked when the tip end of the end effector attached to the robot arm contacts the object to be worked.

It is apparent for a person skilled in the art that many improvements and other embodiments of the present disclosure are possible from the above description. Therefore, the above description is to be interpreted only as illustration, and it is provided in order to teach a person skilled in the art the best mode in which the present disclosure is implemented. Details of one or both of the structures and functions can substantially be changed without departing from the spirit of the present disclosure.

INDUSTRIAL APPLICABILITY

The present disclosure is useful when applying the robot system to the work which requires high precision.

DESCRIPTION OF REFERENCE CHARACTERS

1 Slave Arm (Robot Main Body)
2 Master Arm (Operating Device)
3 Control Device
4 End Effector
5 Force Sensor (Force Sensing Device)
6 Motion Controller
7 Force-sensing Information Processor
8 Monitor Controller
9 Input Device
10 Memory
21 Actual Reaction-force Information Generator
22 Virtual Reaction-force Information Generator
23 Adder
25 Mode Selector
100 Remote Control System (Robot System)
200 Fitting Component
210 Fitted Component
211 Hole
212 Measuring Target Object
213 Measurement Table

What is claimed is:

1. A robot system, comprising:
a robot main body including a robot arm, an end effector attached to the robot arm, and a force sensing device configured to detect a force applied to a tip end of the end effector;
an actual reaction-force information generator configured to generate force-sensing information according to the force detected by the force sensing device, and output the force-sensing information as actual reaction-force information;
a virtual reaction-force information generator configured to output a component of the force detected by the force sensing device, that has a magnitude proportional to a time differentiation value, as virtual reaction-force information;
an adder configured to output information obtained by adding the actual reaction-force information outputted from the actual reaction-force information generator to the virtual reaction-force information outputted from the virtual reaction-force information generator, as synthetic reaction-force information;
an operating device configured to output, when an operator is made to sense a force according to the synthetic reaction-force information outputted from the adder and the operator operates, operating information according to the operation; and
a motion controller configured to control operation of the robot main body according to the operating information outputted from the operating device.

2. The robot system of claim 1, wherein the robot main body is a slave arm and the operating device is a master arm, and the slave arm is remotely controlled by the master arm.

3. The robot system of claim 1, wherein the force sensing device is attached to a base end of the end effector, and is a force sensor configured to detect a force applied to the tip end of the end effector.

4. The robot system of claim 1, further comprising a mode selector configured to be selectable of any one of operating modes of the motion controller to control the operation of the robot main body, the operating modes including:
an automatic mode in which the operation of the robot main body is controlled using a given preset program, without reflecting the operating information in the operation of the robot main body;
a correctable automatic mode in which the operation of the robot main body is controlled using the given preset program, while the operating information is reflectable in the operation of the robot main body; and
a manual mode in which the operation of the robot main body is controlled using the operating information without using the given program,
wherein, when the operating mode is the correctable automatic mode, the motion controller controls the robot main body to perform operation corrected from the operation related to the given program, in response to the operating information while the robot main body operates using the given program.

5. The robot system of claim 1, wherein the robot system is applied to a surgical operation system, and the end effector is a surgical instrument.

6. The robot system of claim 2, further comprising a mode selector configured to be selectable of any one of operating modes of the motion controller to control the operation of the robot main body, the operating modes including:
an automatic mode in which the operation of the robot main body is controlled using a given preset program, without reflecting the operating information in the operation of the robot main body;
a correctable automatic mode in which the operation of the robot main body is controlled using the given preset program, while the operating information is reflectable in the operation of the robot main body; and
a manual mode in which the operation of the robot main body is controlled using the operating information without using the given program,
wherein, when the operating mode is the correctable automatic mode, the motion controller controls the robot main body to perform operation corrected from the operation related to the given program, in response to the operating information while the robot main body operates using the given program.

7. The robot system of claim 3, further comprising a mode selector configured to be selectable of any one of operating modes of the motion controller to control the operation of the robot main body, the operating modes including:
an automatic mode in which the operation of the robot main body is controlled using a given preset program, without reflecting the operating information in the operation of the robot main body;
a correctable automatic mode in which the operation of the robot main body is controlled using the given preset program, while the operating information is reflectable in the operation of the robot main body; and
a manual mode in which the operation of the robot main body is controlled using the operating information without using the given program, wherein, when the operating mode is the correctable automatic mode, the motion controller controls the robot main body to perform operation corrected from the operation related to the given program, in response to the operating information while the robot main body operates using the given program.

8. The robot system of claim 2, wherein the robot system is applied to a surgical operation system, and the end effector is a surgical instrument.

9. The robot system of claim 3, wherein the robot system is applied to a surgical operation system, and the end effector is a surgical instrument.

* * * * *